United States Patent [19]

Pazda et al.

[11] Patent Number: 5,585,730
[45] Date of Patent: Dec. 17, 1996

[54] APPARATUS FOR MEASURING SURFACE CHARGE ON A SHEET OR WEB

[75] Inventors: Robert J. Pazda, Waterloo; Kenneth L. Clum, Webster, both of N.Y.

[73] Assignee: Eastman Kodak Company, Rochester, N.Y.

[21] Appl. No.: 501,856

[22] Filed: Jul. 13, 1995

Related U.S. Application Data

[62] Division of Ser. No. 261,786, Jun. 20, 1994, Pat. No. 5,455,514.

[51] Int. Cl.$^6$ ............................ G01N 27/60; G03G 15/00
[52] U.S. Cl. ...................... 324/452; 324/454; 324/457; 355/216; 361/214
[58] Field of Search .................. 324/452, 454, 324/455, 457, 458, 72, 72.5; 355/216; 361/212, 214

[56] References Cited

U.S. PATENT DOCUMENTS

| | | | |
|---|---|---|---|
| 3,364,423 | 1/1968 | Moulton | 324/454 X |
| 3,787,706 | 1/1974 | De Geest | 361/212 |
| 3,944,354 | 3/1976 | Benwood et al. | 355/216 |
| 4,233,562 | 11/1980 | Blythe | 324/452 X |

OTHER PUBLICATIONS

K. L. Clum and R. J. Pazda, *Journal of Electrostatics*, 24, Segmented Roller: A Device for Measuring Charge Density on a Moving Conducting Web, 1989, pp. 21–32, month unavailable.

K. L. Clum and R. J. Pazda, *Journal of Electrostatics*, 28, The Split Segmented Roller: A Device for Measuring Lateral Charge Distribution on a Moving Web, 1992, pp. 39–45, month unavailable.

*Primary Examiner*—Kenneth A. Wieder
*Assistant Examiner*—Diep Do
*Attorney, Agent, or Firm*—Carl F. Ruoff; Mark G. Bocchetti

[57] ABSTRACT

The present invention is a device for measuring the electric surface charge density on each surface of a sheet. The sheet can either be moving or non-moving. If the sheet is non-moving a pliers-like device having a pair of electrodes aligned opposite with each other is used. The sheet is placed between the electrodes and the surface measurement is made by either one or two electrometers. For a moving web, the apparatus includes a first and second roller each having a charge measurement segment electrically isolated from the roller shell wherein the charge measurement segments periodically engage the web running through the two rollers. Two grounded shields which periodically shield the charge measurement segment are provided. Two electrometers are provided and from this surface charge density measurement and net charge density measurement on the moving sheet are obtained.

4 Claims, 3 Drawing Sheets

APPARATUS FOR MEASURING SURFACE CHARGE ON A SHEET OR WEB

This is a divisional of application Ser. No. 08/261,786, filed 20 Jun. 1994, U.S. Pat. No. 5,455,514.

FIELD OF THE INVENTION

The present invention relates to the field of electrostatic charge measurement. More particularly, this invention relates to the simultaneous independent measurement of electric surface charge on the two surfaces of a non-moving or moving sheet or web.

BACKGROUND OF THE INVENTION

It is desirable to understand electrostatic phenomena observed with moving dielectric and slightly conductive sheets and webs passing over conveyance rollers. For example, it is desirable, in connection with certain coating technologies, especially film manufacturing, to know how much surface charge is on a sheet or web surface just prior to coating.

An apparatus and method for measuring net charge distribution in the lengthwise direction of the web, that is, in the direction of conveyance of the web over the roller, is described in the article entitled "Segmented Roller: A Device for Measuring Charge Density on a Moving Conducting Web" published in the Journal of Electrostatics, Vol. 24, pages 21–32 (1989). Measurement of the charge distribution in the lateral direction of the web is described by the article entitled "The Split Segmented Roller: A Device for Measuring Lateral Charge Distribution on a Moving Web" published in the Journal of Electrostatics, Vol. 28, pages 39–45 (1992) and is the subject of U.S. Pat. No. 5,066,918. While both devices described can measure net charge on a moving web, no capability exists for measuring the polar or bound charge density on the web.

The present invention provides an apparatus capable of measuring surface charge density which is used to determine the polar charge density on a non-moving sheet, and an apparatus with the same capability for a moving sheet or web.

SUMMARY OF THE INVENTION

The present invention is an apparatus for measuring electrostatic surface charge density on a sheet. The apparatus includes a first electrode able to contact a front surface of the sheet and a second electrode electrically isolated from the first electrode and able to contact a back surface of the sheet and aligned with the first electrode. An electrometer is coupled to the first and second electrodes and charge on the front or back surface of the sheet is determined when the sheet is placed between the first and second electrodes. This apparatus can also include a second electrometer wherein the first electrometer is coupled to the first electrode and the second electrometer is coupled to the second electrode. This allows one to determine charge on either surface of the sheet and net charge on the sheet.

The present invention also includes an apparatus for determining surface charge density on a moving web. The apparatus includes a first roller including a roller shell having a first charge measurement segment electrically isolated from the roller shell, the charge measurement segment parallel to the axis of rotation of said first roller. The device also includes a second roller including a second roller shell having a second charge measurement segment electrically isolated from the roller shell, the second charge measurement segment parallel to the axis of rotation of said second roller, the first and second rollers forming a nip wherein the first and second charge measurement segments periodically engage the moving web in an area of surface contact during conveyance of the web through the nip. A first grounded shield which periodically electrically shields the first charge measurement segment during rotation of the first roller is provided along with a second grounded shield which periodically electrically shields the second charge measurement segment during rotation of the second roller. A first and second electrometer are coupled to the first and second charge measurement segments, respectively. The apparatus also includes a control means for measuring charge and storing the measurement by the first electrometer when the first charge measurement segment is in full contact with the web and again when the first charge segment is fully in said grounded shield. The control means also measures charge and stores the measurement by the second electrometer when the second charge measurement segment is in full contact with the web and again when said second charge measurement segment is fully in the second grounded shield.

The present invention, allows one to measure the surface charge density on each surface separately and thus allows determination of the polar charge density on a moving or non-moving web. Heretofore, this was not possible.

For a better understanding of the present invention together with other objects, advantages and capabilities thereof, reference is made to the following description and appended claims in connection with the above-referenced drawings.

DESCRIPTION OF THE PREFERRED EMBODIMENT

Figure 1:
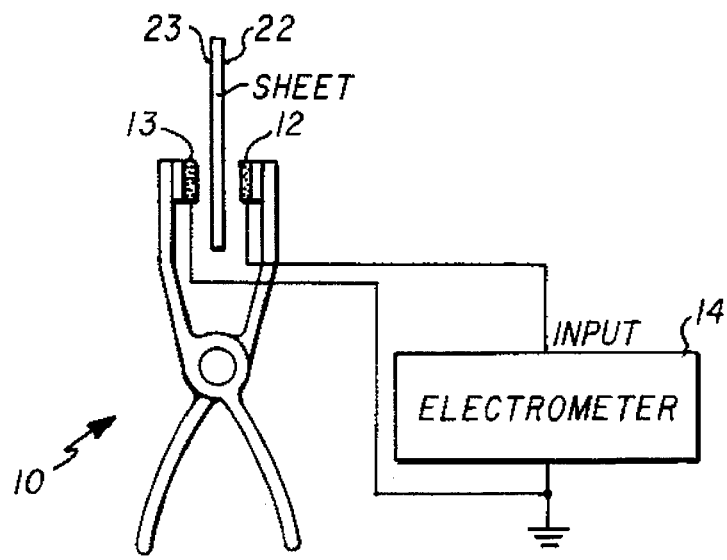
FIG. 1 is a side view of an apparatus for measurement of surface charge density on one surface of a non-moving web using one electrometer.
Figure 2:
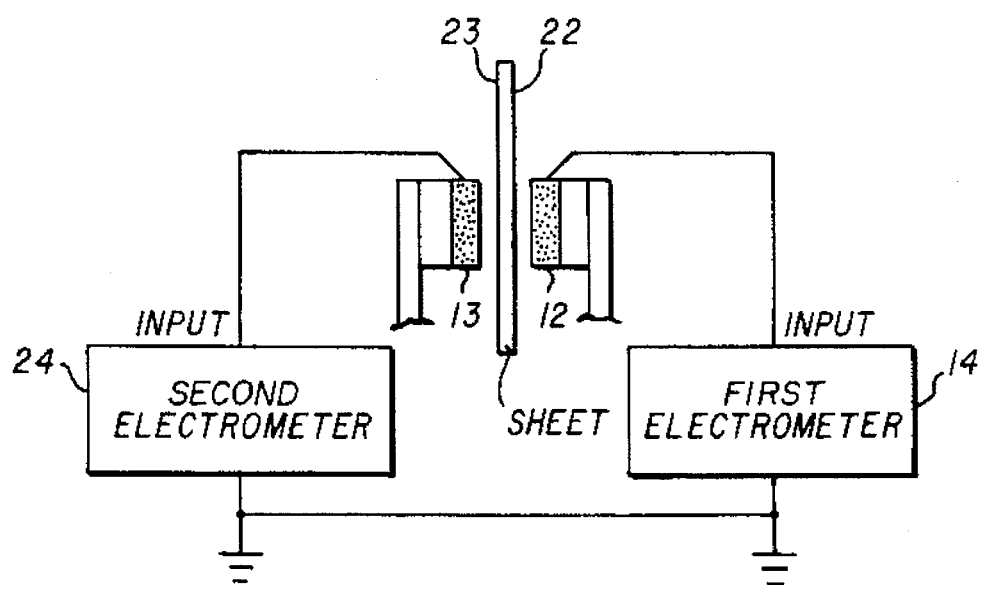
FIG. 2 is a side view of an apparatus for measurement of surface charge density on both surfaces of a non-moving sheet using two electrometers.

Referring to FIGS. 1 and 2 of the drawings, an apparatus for measuring surface charge density on a non-moving sheet, such as photographic film, is shown. The apparatus includes a pliers-like device 10 having two conductive electrodes 12, 13 which are electrically isolated from each other and the pliers. The electrodes can be made from any conductive material but preferably would be of a pliable conductive rubber to conform to the surface which they contact. The sheet to be measured is placed between the two electrodes such that the first electrode is in intimate contact with a first surface of the sheet and the second electrode is in intimate contact with a second surface of the sheet. The first and second electrodes are aligned with each other. The portion of the surface charge on the first surface of the sheet that lies directly underneath the first electrode is imaged in the first electrode and the portion of the surface charge on the second surface of the sheet that lies directly underneath the second electrode is imaged in the second electrode.

FIG. 1 shows the apparatus for measuring the surface charge on one surface of a sheet or web. One electrometer 14 is coupled to the first electrode 12 and the ground connection of the electrometer coupled to the second electrode 13. The image charge on the first electrode 12 comes from the electrometer and a reading is given by the electrometer which is equal in magnitude and sign to the charge on the first surface 22. The image charge on the second electrode 13 comes from ground and allows for an accurate charge measurement on the first surface 22. Charge on the second surface 23 is measured by the same device by reinserting the sheet between the electrodes, this time having the first electrode 12 in contact with the second surface 23.

FIG. 2 shows the measurement of surface charge using two electrometers 14, 24 with the first electrode 12 coupled to the first electrometer 14 and the second electrode 13 coupled to the second electrometer 24. The amount of charge on each surface 22, 23 is imaged in each electrode 12, 13 which produces a reading on each electrometer 14, 24 equal in magnitude and sign to the charge on each surface. The net charge of the sheet is determined by adding together the charge on the first surface 22 and the charge on the second surface 23. The polar charge on the sheet is determined by taking the lesser absolute value of the charge on the first surface 22 and the charge on the second surface 23 if the charge on the first and second surfaces are of opposite signs.

For example, if the charge on the first surface is 10 nC and the charge on the second surface is −7 nC, then the polar charge on the sheet is 7 nC and net charge on the sheet is 3 nC. If the charge on both surfaces is the same sign, there is no polar charge on the sheet.

In accordance with this invention, therefore, an apparatus for measuring polar charge density on a non-moving sheet is disclosed. The device has two electrically conductive electrodes aligned with each other and electrically isolated from each other. When a sheet is placed between the electrodes, the electrodes contact each surface of the sheet and the amount of charge on the sheet is measured. The device can include either one electrometer or two electrometers. In the preferred mode, using two electrometers, the amount of charge on each sheet in the area of electrode contact is imaged on each electrode which produces a reading on the respective electrometer. The amount of polar charge density on the sheet is then determined by considering both electrometer measurements. The device can also measure net charge on a sheet. In most practical applications there is normally a combination of both polar and net charge. The device can uniquely specify the amount of each.

Figure 3:
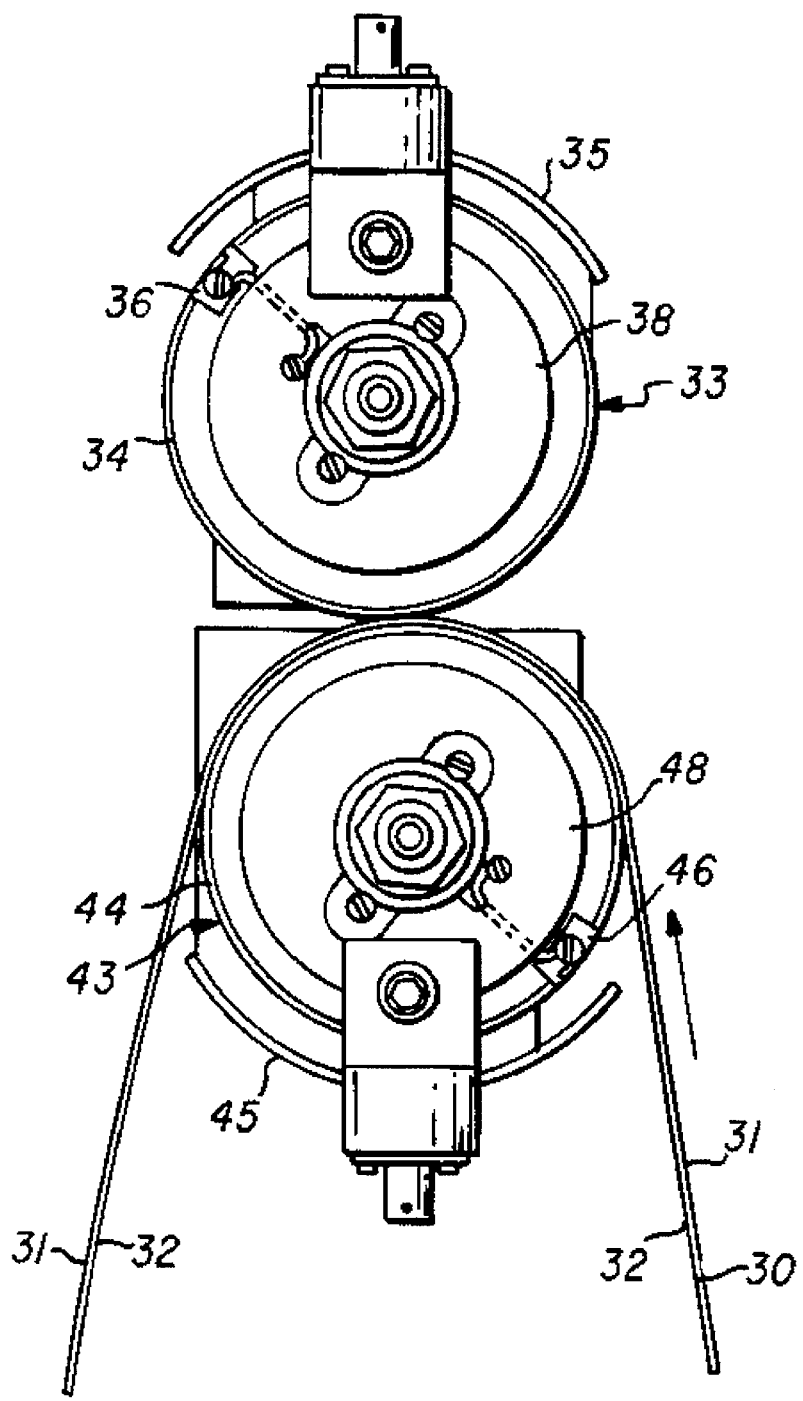
FIG. 3 is a side view of an apparatus for measurement of surface charge density on a moving web.
Figure 4:
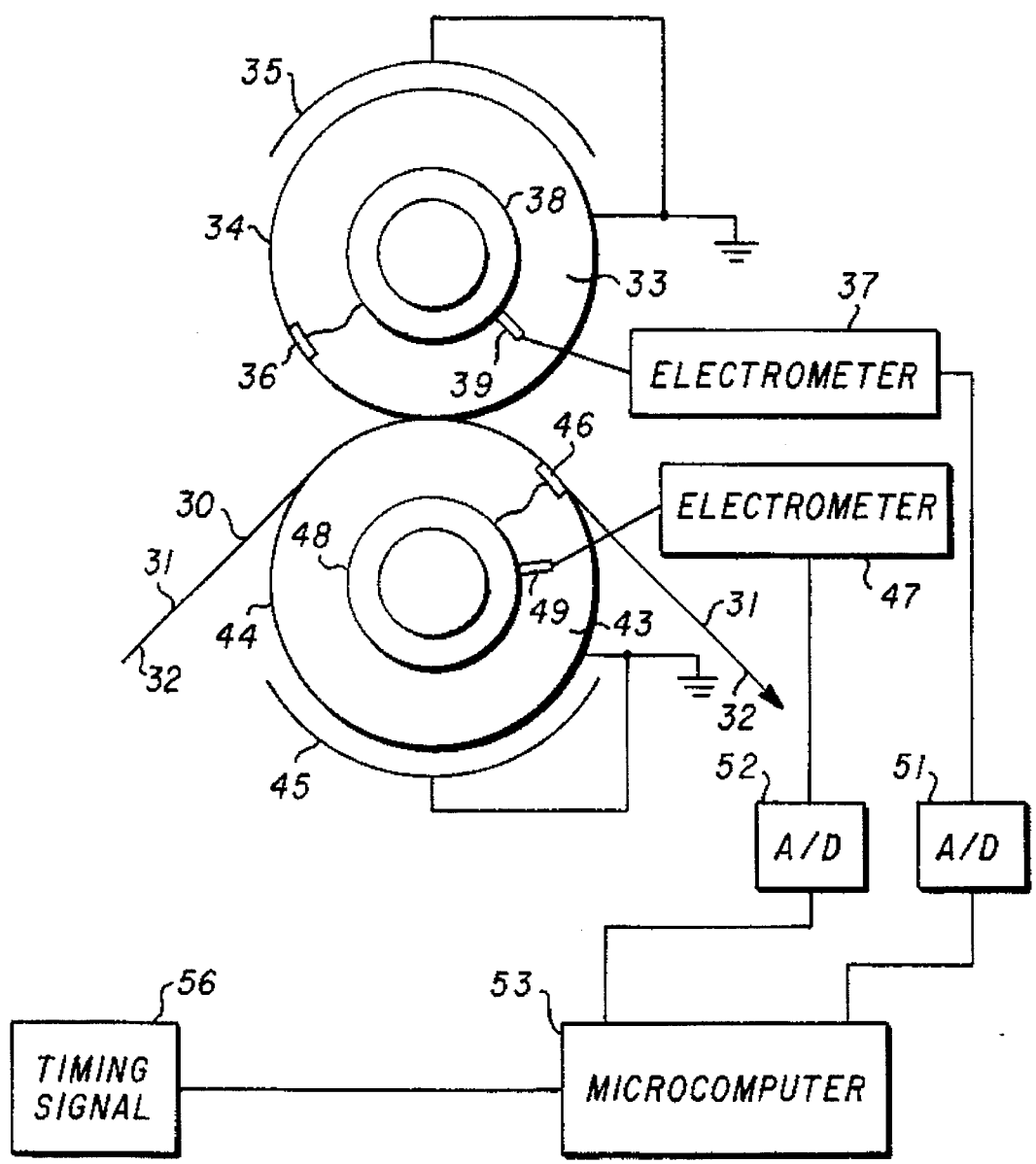
FIG. 4 is a schematic illustration of the measurement apparatus of FIG. 3 useful in explaining the operation of the invention.

Referring to FIGS. 3 and 4 of the drawings, an apparatus for separately measuring the surface charge density on the two surfaces of a moving sheet or web 30 such as photographic film or paper is shown. The apparatus includes a first cylindrical roller 33 having an outer surface or shell 34 that includes one or more charge measurement segments 36 on or part of the outer surface 34 partially covered by a stationary semi-cylindrical electrical grounded shield 35. The electrically grounded shell 34 and charge measurement segment 36 may be made of any conductive material such as stainless steel or rubber and are electrically isolated from each other. If more than one segment is provided, the segments are electrically isolated from each other.

The apparatus also includes a second roller 43 having an outer surface or shell 44 partially covered by a stationary semi-cylindrical electrically grounded shield 45. The outer roller surface 44 includes at least one charge measurement segment 46. The electrically grounded shield 45 and charge measurement segment 46 are electrically isolated from each other. Each charge measurement segment 36, 46 is coupled to an electrometer 37, 47, respectively.

The roller arrangement is such that in operation, a web is wrapped around a portion of one roller surface 44 and is typically conveyed between a supply and take up reels (not shown) and held in tension around one roller by means of tension rollers (not shown) preferably mounted remotely on a back plane (not shown). When a sheet or web 30 is wrapped around the outer surface 44 of roller 43 in this manner, and the roller 43 rotates with conveyance of the sheet or web 30, segments 36 and 46 on both rollers 33 and 43, respectively, periodically contact the web 30. The semi-cylindrical grounded shields 35 and 45 are mounted on support brackets (not shown) to provide a shielded environment for the segments 36 and 46 during a portion of each revolution of the rollers 33 and 43. This permits measurement of the charge on the segments 36 and 46 independent of the effects of charge on the sheet or web. The necessity of this measurement is explained more fully in The Journal of Electrostatics Articles referred to in the background of the invention section.

Segment 36 is electrically coupled to slip ring 38, and segment 46 is electrically coupled to slip ring 48. The slip rings 38 and 48 are electrically connected by means of contact fingers 39 and 49 to external electrometers 37 and 47, respectively. Charge on the two web surfaces 31, 32 where complete contact is made with the measurement segments 36, 46 produces an equal charge at the electrometer inputs by induction. At full contact of each measurement segment 36, 46 to each web surface 31, 32, a timing signal means 56 causes the electrometer outputs to be recorded.

In operation, with reference to the schematic illustration of FIG. 4, a web 30 is conveyed over the outer surface 44 of the rotating roller 43 contacting surface 32 and with the outer surface 34 of roller 33 contacting surface 31 of web 30. The segments 36, 46 periodically contact the web surfaces 31 and 32. The voltage outputs of the electrometers are converted to digital form by analog to digital converters 51 and 52 for application to a microcomputer 53 for data storage and analysis. A timing signal means 56 causes the electrometer outputs to be recorded. The surface charge is calculated using both measurements when the segment is in the shield and against the sheet or web and is equal to the amount of charge measured on the segment in full contact with the surface minus the charge measured on the segment in the shield before contact. In this manner a measure of the surface charge on both surfaces is obtained at intervals equal to the roller circumference.

The polar charge density on a moving sheet or web is determined by taking the lesser absolute value of the charge density on the first surface 31 and the charge density on the second surface 32 if the first surface and second surface charge densities are of opposite sign. The net charge density on the moving sheet is determined by adding the surface charge on the first surface to the surface charge density on the second surface.

Referring again to FIG. 4 of the drawings, the electrically isolated measurement segments are shown at a random position. Although operative, the segments positioned in this manner do not allow for optimum accuracy. For maximum measurement precision, the segments should be synchronized such that both are in contact with the moving web simultaneously. For example, when the top roller segment 36 is in the six o'clock position, the bottom roller segment 46 would be in the twelve o'clock position. Roller synchronization could be achieved mechanically in a number of different ways, an example being a gear mounted to the side of each roller of identical diameter linked together via a gear belt.

Multiple segments could easily be implemented on each roller if the measurement of polar charge is desired at distances in the lengthwise direction which are less than the roller circumference.

While there has been shown and described what are at present considered the preferred embodiments of the invention, it will be obvious to those skilled in the art the various changes, alterations and modifications may be made therein without departing from the scope of the invention as defined by the appended claims.

What is claimed is:

1. An apparatus for determining charge on a sheet comprising:

a first electrode to contact a front surface of the sheet;

a second electrode electrically isolated from the first electrode to contact a back surface of the sheet and aligned with said first electrode; and an electrometer coupled to said first and second electrodes wherein charge on a selected one of the front and back surfaces of the sheet is determined when the sheet is placed between said first and second electrodes.

2. An apparatus for determining charge on a sheet comprising:

a first electrode to contact a front surface of the sheet;

a first electrometer coupled to said first electrode;

a second electrode electrically isolated from said first electrode to contact a back surface of the sheet aligned with said first electrode; and a second electrometer coupled to said second electrode wherein the charges on the front and back surfaces of the sheet are determined by placing the sheet between said first and second electrodes.

3. The apparatus according to claim 2 wherein net charge of the sheet is determined by adding together the charge on the front surface and the charge on the back surface.

4. The apparatus according to claim 2 wherein the polar charge on the sheet is determined by taking the lesser absolute value of the charge on the front surface and the charge on the back surface if the charge on the front surface and the charge on the back surface are of opposite signs.

* * * * *